United States Patent
Dumanli Oktar

(10) Patent No.: US 12,224,807 B2
(45) Date of Patent: Feb. 11, 2025

(54) SYSTEM AND METHOD WHICH PROVIDES WIRELESS COMMUNICATION BETWEEN BIO-NANO ELEMENTS AND MACRO/MICRO DEVICES

(71) Applicant: BOGAZICI UNIVERSITESI, Istanbul (TR)

(72) Inventor: Sema Dumanli Oktar, Istanbul (TR)

(73) Assignee: BOGAZICI UNIVERSITESI, Istanbul (TR)

( * ) Notice: Subject to any disclaimer, the term of this patent is extended or adjusted under 35 U.S.C. 154(b) by 490 days.

(21) Appl. No.: 17/785,936

(22) PCT Filed: Dec. 21, 2020

(86) PCT No.: PCT/TR2020/051338
§ 371 (c)(1),
(2) Date: Jun. 16, 2022

(87) PCT Pub. No.: WO2021/126135
PCT Pub. Date: Jun. 24, 2021

(65) Prior Publication Data
US 2023/0027600 A1    Jan. 26, 2023

(30) Foreign Application Priority Data

Dec. 20, 2019 (TR) ................................. 2019/20978
Dec. 19, 2020 (TR) ................................. 2020/20960

(51) Int. Cl.
| | | |
|---|---|---|
| H04B 13/00 | (2006.01) | |
| A61K 41/00 | (2020.01) | |
| H01Q 1/27 | (2006.01) | |
| H01Q 1/36 | (2006.01) | |

(Continued)

(52) U.S. Cl.
CPC ....... *H04B 13/005* (2013.01); *A61K 41/0028* (2013.01); *H01Q 1/273* (2013.01);
(Continued)

(58) Field of Classification Search
CPC .. H04B 13/005; A61K 41/0028; H01Q 15/00; H01Q 1/273; H01Q 1/36;
(Continued)

(56) References Cited

U.S. PATENT DOCUMENTS

| | | |
|---|---|---|
| 10,265,017 B1 | 4/2019 | Myslinski |
| 2017/0346512 A1 | 11/2017 | Chae et al. |

(Continued)

FOREIGN PATENT DOCUMENTS

| | | |
|---|---|---|
| EP | 1850513 B1 | 1/2010 |
| KR | 101614653 B1 | 4/2016 |

OTHER PUBLICATIONS

Luca Felicetti, et al., Applications of molecular communications to medicine: a survey, Nano Communication Networks, 2015.

(Continued)

*Primary Examiner* — Keith Ferguson
(74) *Attorney, Agent, or Firm* — Bayramoglu Law Offices LLC

(57) ABSTRACT

A system for receiving data from the nano-elements inside the body or on the body is provided, including a molecular communication unit. The molecular communication unit includes an antenna to be attached to the body or on the body in order to transfer the data from the inside of the body to the outside of the body and an antenna body configured to change and reflect an electromagnetic signal when the antenna is subjected to electromagnetic signal, and the antenna body includes a re-shapeable part made of a material which changes in form when it is subjected to a factor inside the body. A system for sending data to nano-elements is also provided.

33 Claims, 5 Drawing Sheets

(51) Int. Cl.
    *A61B 5/07*        (2006.01)
    *B82Y 5/00*        (2011.01)
(52) U.S. Cl.
    CPC .................. *H01Q 1/36* (2013.01); *A61B 5/07* (2013.01); *A61B 2562/0285* (2013.01); *B82Y 5/00* (2013.01)
(58) Field of Classification Search
    CPC ... A61B 5/07; A61B 5/073; A61B 2562/0285; A61B 2562/028; B82Y 5/00
    See application file for complete search history.

(56)              References Cited

U.S. PATENT DOCUMENTS

2019/0374666 A1* 12/2019 Arndt ..................... H05B 6/80
2020/0268256 A1*  8/2020 Harding ............... A61B 5/0295

OTHER PUBLICATIONS

Baris Atakan, et al., Body Area NanoNetworks with Molecular Communications in Nanomedicine, IEEE Communications Magazine, 2012, pp. 28-34.
Derya Malak, et al., Molecular communication nanonetworks inside human body, Nano Communication Networks, 2012, pp. 19-35, vol. 3.
Sema Dumanli, On-Body Antenna with Reconfigurable Radiation Pattern, IEEE MTT-S International Microwave Workshop Series on RF and Wireless Technologies for Biomedical and Healthcare Applications, 2014.

* cited by examiner

SYSTEM AND METHOD WHICH PROVIDES WIRELESS COMMUNICATION BETWEEN BIO-NANO ELEMENTS AND MACRO/MICRO DEVICES

CROSS REFERENCE TO THE RELATED APPLICATIONS

This application is the national phase entry of International Application No. PCT/TR2020/051338, filed on Dec. 21, 2020, which is based upon and claims priority to Turkish Patent Applications No. 2019/20978, filed on Dec. 20, 2019, and No. 2020/20960, filed on Dec. 19, 2020, the entire contents of which are incorporated herein by reference.

TECHNICAL FIELD

The present invention relates to a system which provides data exchange between nano-elements provided inside the body or on the body and the macro/micro-elements provided inside the body or on the body and which provides data transfer from the molecular nano communication network to the body area network, and a method where said system is applied.

BACKGROUND

Nano-elements like nano-machine, nano-drug, bacterium existing in the body communicate with each other by means of messenger molecules.

In the EPO application with number EP1850513B1, nano-machines which communicate with each other by means of molecules are described.

In order to trace the events in the body instantaneously, nano-elements must be able to communicate with a device existing outside the body. Communication of the nano-elements inside the body with the devices outside of the body can be used for the purposes of diagnosis, treatment and sensing. In the present art, agent devices are known which have nano-sensor and which transmit the data, received from the nano sensor, to an external communication unit (for instance, a Body Area Network (BAN)) outside of the body.

In the document of L. Felicetti et al, "Applications of molecular communications to medicine: A survey, "Nano Communication Networks 7 (2016) 27-45, a method is described which comprises a nano-sensor which senses the messenger molecules used by the nano-elements for providing data exchange between nano-elements in the vein and communication unit outside the body, and a processor which processes the data taken from the nano-sensor and a prop inserted into the vein for receiving data from the processor. However, this method is not suitable for communicating with nano-elements and moreover, prop has to be inserted into the vein when data is desired to be taken.

As a result, because of all of the abovementioned problems, an improvement is required in the related technical field.

SUMMARY

The present invention relates to a communication system and method, for eliminating the above mentioned disadvantages and for bringing new advantages to the related technical field.

An object of the present invention is to provide a system and method which provide communication between the nano-elements inside or on body and micro/macro electronic devices outside or inside body.

Another object of the present invention is to provide a system and method which provide communication between the nano-elements inside or on body and micro/macro electronic devices outside or inside body without needing a power supply inside or on the body.

Another object of the present invention is to provide a system and method which provide communication between the nano-elements inside or on the body and micro/macro electronic devices outside or inside the body in a wireless manner.

Another object of the present invention is to provide a system and method where the communication element, placed into the body for communication, is not required to be removed from the body by means of surgical operation after the communication finishes.

Another object of the present invention is to provide a system and method where the harm, given to the body by the communication element placed into or on the body for communication, is reduced.

Another object of the present invention is to provide a system and method which communicate with the nano-elements inside or on the body and which provides diagnosis and treatment.

In order to realize the abovementioned objects and the objects which are to be deducted from the detailed description below, the present invention is a system for receiving data from the nano-elements inside or on the body. Accordingly, the improvement is that said system comprises a molecular communication unit comprising an antenna to be attached into or on the body for transferring data from the inside or through the body to the outside of the body and said antenna comprises an antenna body configured to transform and reflect electromagnetic signals it is exposed to, and said antenna body comprises a re-shapeable part made of a material which changes in form when it is subjected to a factor inside or on the body. As the form of the antenna changes, resonance frequency changes and thus, this frequency is sensed by another communication unit, and data can be transferred from inside of the body or through the body to outside of the body. Since passive antenna is used and since the antenna shows change according to the factors inside body, there remains no need for power supply, cable, prop, etc.

In another preferred embodiment of the present invention, another communication unit is provided having a receiver/transmitter for transmitting electromagnetic signal to the antenna and for receiving the electromagnetic signal reflected by the antenna and a processor unit configured to control transmitting of electromagnetic signal to the antenna by said receiver/transmitter and to receive electromagnetic signal received from the receiver/transmitter and where said processor unit is configured to determine whether it is subjected to a factor from a region inside or on the body according to at least one characteristic property of the electromagnetic signal received from the antenna. Thus, the form change in the antenna is detected, and the data, sent by the nano-elements, can be taken without needing a power supply, cable, prop in a region inside or on the body.

In a preferred embodiment of the present invention, whole of said antenna body is the re-shapeable part.

In another preferred embodiment of the present invention, said material, which changes form when it is subjected to a factor inside the body, is bio-degradable material. Thus, without needing a surgical operation, the antenna is bio-degraded in the body and removed from the body.

In another preferred embodiment of the present invention, said material, which can change form when it is subjected to a factor on the body, is preferably provided in an embodiment which is similar to a bio-degradable vessel, sheath, etc.

In another preferred embodiment of the present invention, a bio-film is provided which at least partially wraps the re-shapeable part.

In another preferred embodiment of the present invention, the re-shapeable part comprises a material of which the bio-degradation speed increases when it is subjected to a first substance.

In another preferred embodiment of the present invention, said system comprises a genetically engineered microorganism for generating the bio-film which generates said first substance when subjected to a messenger molecule. Thus, when the messenger molecule comes in contact with the bio-film from the nano-elements, the genetically engineered microorganism produces the first substance and provides the re-shapeable part to be subjected to bio-degradation.

In another preferred embodiment of the present invention, said messenger molecule is quorum sensing molecule related to a bacteria infection and when the genetically engineered microorganism is subjected to said quorum sensing molecule, it is *Coli* Bacilli strain which produces acidic acid as the first substance. Thus, the system can be used for diagnosis, and data, related to this, can be sent to the outside of the body in case of bacteria infection.

In another preferred embodiment of the present invention, said bio-degradable material is selected from bio-materials which are suitable for use inside or on the body. It is preferably selected from magnesium, iron and double-layered zinc/iron.

In another preferred embodiment of the present invention, at least one substrate is provided in a manner at least partially wrapping the antenna for decelerating the degradation speed of the re-shapeable part. Thus, the duration where the antenna is desired to stay in the body in working condition can be increased.

In another preferred embodiment of the present invention, said substrate comprises bio-degradable material.

In another preferred embodiment of the present invention, said substrate comprises preferably at least one of polyglycerol sebacate, polyoctamethylene meleate (anhydrite) citrate, polylactic acid and poly(lactic-co-glycolic acid).

In another preferred embodiment of the present invention, for adjusting the bio-degradation speed of said substrate, the coating thickness is selected from one of the predetermined thicknesses in accordance with the targeted degradation speed.

In another preferred embodiment of the present invention, two substrates are provided in a manner taking the antenna in between in usage in the body. Thus, whole of the molecular communication unit is degraded in the body and the need for removal thereof by means of surgical operation is eliminated.

In another preferred embodiment of the present invention, said re-shapeable part is configured to bend when it is subjected to a force which exceeds a predetermined threshold value.

In another preferred embodiment of the present invention, a genetically engineered tissue is provided which is related to the re-shapeable part which provides deformation of the re-shapeable part by straining and by applying force to the re-shapeable part when it is subjected to a messenger molecule.

In another preferred embodiment of the present invention, said genetically engineered tissue is muscle tissue. Thus, the antenna can be deformed without needing external energy.

In another preferred embodiment of the present invention, the other communication unit comprises a memory unit provided in an associated manner with the processor unit in a manner permitting reading data by the processor unit; and the processor unit is configured to determine whether the antenna is subjected to a factor inside the body or on a region of the body according to the deviation of the characteristic properties of the signal, received from the antenna, from at least one characteristic property existing in the memory unit.

In another preferred embodiment of the present invention, said characteristic property is frequency. Thus, the deviation of the antenna in the resonance frequency is detected and it is detected whether the messenger molecules are taken or not.

In another preferred embodiment of the present invention, the other external communication unit comprises an input output unit which provides the processor unit to realize an output related to subjecting of the antenna to a factor inside the body or on a region on the body.

In another preferred embodiment of the present invention, the other external communication unit comprises a device body and said device body is placed inside or on the body.

In another preferred embodiment of the present invention, the antenna body comprises a first part, a second part connected to said first part by means of a first re-shapeable part and a third part connected to said second part by means of a second re-shapeable part.

In another preferred embodiment of the present invention, the first re-shapeable part and the second re-shapeable part are made of bio-degradable materials which are degraded when they are subjected to factors which are different from each other.

In another preferred embodiment of the present invention, the first re-shapeable part and the second re-shapeable part are coated with substrate having bio-degradation speeds which are different from each other or are coated with the same bio-degradable material having different thicknesses. Different parts of the antenna respond to different messenger molecules and the signal received from the antenna is examined and the data related to which messenger molecule is taken is received and thus, the data transfer bandwidth is increased.

The present invention is moreover a method for receiving data from the nano-elements inside the body or a region on the body. Accordingly, the improvement is that the method comprises the following steps:

a processor unit transmits an interrogation signal to an antenna having an antenna body configured to reflect electromagnetic signal when it is subjected to electromagnetic signal by means of a receiver/transmitter and a re-shapeable part made of a material which can change form when said antenna body is subjected to a factor inside the body or a region on the body, said processor unit receives a response signal, the reflected interrogation signal by the antenna, by means of said receiver/transmitter, the processor unit determines whether the antenna is subjected to a factor inside the body or a region on the body according to the deviation of the characteristic properties of the received response signal from the predetermined reference characteristic properties.

The present invention is moreover a system for transferring data to the nano-elements which communicate with the messenger molecules in the body or a region on the body.

Accordingly, the improvement of the subject matter system is that an external communication unit is provided to be attached to the body or to a region on the body and having an antenna configured to produce heat when it is subjected to an electromagnetic signal, and a bio-film associated with said antenna and accommodating a genetically engineered microorganism which produces messenger molecule when a predetermined temperature level is reached.

In another preferred embodiment of the present invention, an external communication unit is provided having a receiver/transmitter for transmitting electromagnetic signal to the antenna and for receiving the electromagnetic signal reflected by the antenna and a processor unit configured to control transmission of electromagnetic signal to the antenna of said receiver/transmitter and where said processor unit is configured to detect the resonance frequency of the antenna according to the response signal of the antenna reflected in correspondence with an interrogation signal sent by the receiver/transmitter and when data is to be sent to the nano-element, the processor unit is configured to transmit an electromagnetic heating signal to the antenna in continuous and monolithic form at the detected resonance frequency. Thus, data transfer is provided from micro/macro devices to the nano-elements inside the body.

In another preferred embodiment of the present invention, said antenna body is made of a bio-degradable material with increasing bio-degradation speed as temperature increases, and the processor unit is configured to receive a response heating signal which is the reflected form of said heating signal and to stop the heating process in case it detects that the characteristic properties of the response heating signal deviates from the predetermined reference characteristic properties at the predetermined amount. Thus, when data transfer is completed, heating process is stopped.

The present invention is moreover a method for transferring data to the nano-elements which communicate with the messenger molecules in the body or on a region of the body. Accordingly, the improvement is that the method comprises the following steps:
 the processor unit receives a data transfer command as input,
 the processor unit transmits electromagnetic wave to an antenna which reflects the electromagnetic wave reflected falling thereon, when electromagnetic wave falls thereon by means of a receiver/transmitter,
 the processor unit determines the resonance frequency of the electromagnetic waves reflected by the antenna by means of the receiver/transmitter,
 the processor unit transmits continuous and monolithic electromagnetic signal to the antenna at the determined resonance frequency for increasing the temperature of a bio-film comprising genetically engineered microorganism provided in the vicinity of the antenna and producing a messenger molecule when the temperature increases to the predetermined level at the determined resonance frequency.

In another preferred embodiment of the present invention, information is transferred to the from micro/macro devices to the molecular communication inside or on the body. In this embodiment, there is a bio-degradable capsule placed inside or on the body. The capsule comprises the molecules which are to be used in molecular communication. When the capsule wall is subjected to the electromagnetic signal sent from outside of the body, it is degraded because of heat increase and leads to release of messenger molecule.

In another preferred embodiment of the present invention, said antenna body is made of a bio-degradable material with increasing degradation speed as temperature increases,
 the processor unit receives the response signal produced by reflecting continuous and monolithic electromagnetic signal at resonance frequency by the antenna by means of the receiver/transmitter,
 the processor unit stops transmitting electromagnetic signal in case it detects that the response signal characteristic properties deflect from the predetermined reference characteristic properties at a predetermined amount.

REFERENCE NUMBERS

Figure 1:
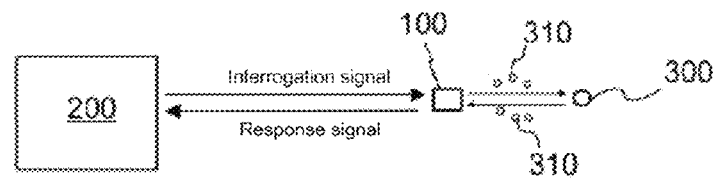
FIG. 1 is a representative view of the subject matter system for usage inside the body.

100 Molecular communication unit
110 Antenna
111 Antenna body
112 Re-shapeable part
113 First part
114 Second part
115 Third part
117 First re-shapeable part
118 Second re-shapeable part
120 Bio-film
121 Genetically engineered microorganism
122 First substance
130 Substrate
140 Genetically engineered tissue
200 Other communication unit
210 Processor unit
220 Receiver/transmitter
230 Memory unit
240 Input/output unit
300 Nano-element
310 Messenger molecule
400 External device

DETAILED DESCRIPTION OF THE EMBODIMENTS

In this detailed description, the subject matter is explained with references to examples without forming any restrictive effect only in order to make the subject more understandable.

With reference to FIG. 1, the present invention is a molecular communication unit (100), which is a preferred method of the present invention, which functions as a gateway for the communication between nano-elements (300) in the body and the other communication unit outside the body and a system comprising this molecular communication unit.

The nano-elements (300) mentioned here describe the elements which communicate with the messenger molecules (310) in the body. The nano-elements (300) can be cells like bacteria, etc or human-made elements like nano-drug, nano-machine, etc. The network formed by nano-elements (300) by means of communicating with each other is known as Molecular Nano Communication Network (MNCN) in the art.

The messenger molecules (310) describe the molecules produced or received by the nano-elements (300). For instance, a nano-element (300) produces messenger molecule (310) and transmits signal to the other nano-elements (300) or to the other cells. In another example, when a bacterium leads to infection, it may generate messenger molecule (310).

The subject matter system basically detects messenger molecules (310) in usage or outside of the body thanks to the molecular communication unit (100) and provides production of a signal accordingly, and the other communication unit (200) receives this signal and realizes the part of the communication which is from inside of the body or from a region on the body to outside of the body and the other communication unit (200) transmits a signal to the molecular communication unit (100), and messenger molecules (310) are produced by the molecular communication unit (100) and the part of the communication from the outside of the body to the inside of the body or a region on the body is realized. The novel structure of the molecular communication unit (100), whose details are given below, provides the data transfer from the outside of the body to the inside of the body and from the inside of the body to the outside of the body without needing any power source like battery in the body.

Figure 2A:
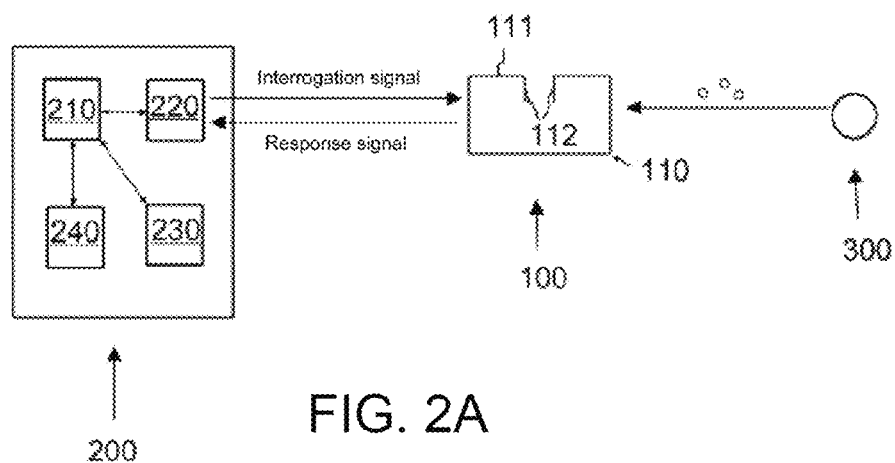
FIG. 2A is a representative view of the system, for usage inside the body, which transmits data from inside the body to outside of the body.

In FIG. 2A, the structure of the molecular communication unit (100) is given which transfer data from the nano-elements (300) inside the body or a region on the body to the other communication unit (200) outside the body. The molecular communication unit (100) in this possible embodiment comprises an antenna having an antenna body (111) which reflects electromagnetic signal according to the electromagnetic signal it receives. As also known in the art, said antenna body (111) operates in a similar manner to the antenna of the passive RFID tag. In other words, the antenna body (111) is arranged to make communication with back reflection. The antenna body (111) generates a response signal according to the type of the electromagnetic signal being subjected to and according to its own form.

The antenna body (111) comprises a re-shapeable part made of a material which changes shape when at least one part of the antenna body (111) is subjected to at least one factor inside the body.

In this possible embodiment of the present invention, whole of the antenna body (111) comprises the re-shapeable part. When the re-shapeable part is subjected to a factor in the body, the form of said re-shapeable part changes and the electromagnetic signal produced by the antenna changes and the antenna indirectly transmits information related to this change and provides data flow from inside of the body or a region on the body to the outside of the body.

The other communication unit (200) of the system comprises a receiver/transmitter (220) for transmitting electromagnetic signal to the antenna and for receiving the response reflected by the antenna. Said receiver/transmitter (220) operates in wide band and comprises an adjustable antenna (not illustrated in the figures) and other components known in the art which are needed for digitalizing for distributing/receiving electromagnetic waves. The other communication unit (200) comprises a processor unit (210) for controlling the receiver/transmitter (220) and for processing the electromagnetic signals received by the receiver/transmitter (220). The other communication unit (200) also comprises a memory unit (230) where the processor unit (210) can read and write data. The other communication unit (200) can moreover comprise an input/output unit (240) which provides inputting data to the processor unit (210) and which provides transfer of data outwards by the processor unit (210). The input/output unit (240) can be ports of peripheral units like keyboard, mouse, screen, etc. and wireless communication module, etc. In a possible embodiment, the other communication unit (200) is configured to be connected to a Body Area Network (BAN) or to other external devices (400). In a possible embodiment, the other communication unit (200) comprises a body and said body is provided in a wearable form. Said body can be in the form of a wristband, watch, etc. and can also be placed in the body.

During transfer of data from inside or on body to the outside of the body, the other communication unit (200) functions as follows:

The processor unit (210) provides transmission of an interrogation signal to the antenna by means of a receiver/transmitter (220). The antenna (111) generates a response signal by reflecting the interrogation signal. The processor unit (210) receives the response signal by means of the receiver/transmitter (220). The processor unit (210) evaluates the characteristic properties of the response signal. Said characteristic properties can be amplitude, frequency, etc. The processor unit (210) determines that data (for instance bit "1") comes from the antenna in case the processor unit (210) detects that the characteristic properties of the response signal deviate from the predetermined reference characteristic properties, and the processor unit (210) provides completing of the process of taking data from inside of the body or from a region on the body.

In more details, the processor unit (210) can access a table or graphic (shown as example in FIG. 11) recorded in the memory unit (230) and including the reference characteristic properties of the response signals which has to be sent by the antenna or which is expected to be sent by the antenna with respect to the depth of the antenna or with respect to time as from the time where the antenna is placed under normal conditions. When it is detected that the characteristic properties of the response signal realize deviation in said table or in the graphic, it is detected that the re-shapeable part of the antenna is deformed or deformed more than expected and that the messenger molecules (310) reach the antenna; and data is produced related to this. Thus, in the body, the communication molecules produced by the nano-elements (300) are sensed and are transferred to outside of the body. This can be used for the aims of communication, sensing, diagnosis, etc.

In this possible embodiment of the present invention, the re-shapeable part is made of a bio-degradable material. When the re-shapeable part (112) is subjected to predetermined messenger molecules (310), the bio-degradation speed increases and thus, the speed of change of the electromagnetic signal reflected during normal bio-degradation becomes different. Said body factor can be messenger molecules (310) produced by a bacteria infection, heat change formed by the messenger molecules (310) or the chemical change formed by the messenger molecules (310).

Figure 2B:
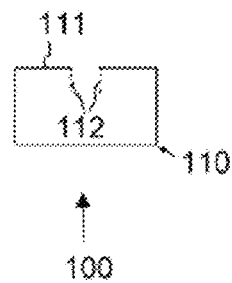
FIG. 2B is a representative view of the partial bio-degraded form of the re-shapeable part of the antenna of the communication unit which transmits data from inside the body to outside of the body, for usage inside the body.
Figure 2C:
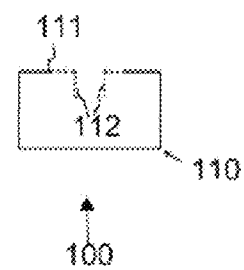
FIG. 2C is a representative view of the partial bio-degraded form of the re-shapeable part of the antenna of the communication unit which transmits data from inside the body to outside of the body, for usage inside the body.

In FIG. 2B, the representative view of the partial bio-degraded form of the re-shapeable part of the antenna body (111) is given, and in FIG. 2B, the representative view where bio-degradation is greater is given. The electromagnetic signal, reflected by the antennas in FIG. 2A, FIG. 2B and FIG. 2C, will be distinguishably different from each other since the form of the antenna changes and thus since the resonance frequency changes.

Figure 3:
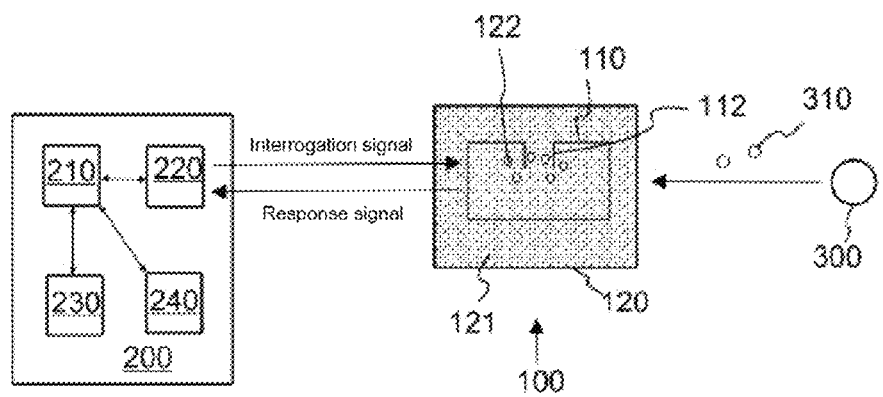
FIG. 3 is a representative view of a possible embodiment of the communication unit which transmits data from inside the body to outside of the body and the system comprising said communication unit, for usage inside the body.

In FIG. 3, another possible embodiment of the communication unit which transfers data from inside of the body to outside of the body is given. The communication unit comprises an antenna having an antenna body (11) which reflects electromagnetic signal according to the electromagnetic signal it receives. The antenna body (111) comprises a re-shapeable part made of bio-degradable material. The re-shapeable part (112) is made of a bio-degraded material or a material with increasing bio-degradation speed when said re-shapeable part is subjected to a first substance (122) or substances which have an effect which is similar to the effect of the first substance (122).

The bio-degradable material can be magnesium, iron and double-layered zinc/iron, etc.

The molecular communication unit (100) comprises a bio-film (120) provided in a manner at least partially wrapping the re-shapeable part of the antenna body (111). Said bio-film (120) is formed by genetically engineered microorganism (121) which produces a first substance (122) when subjected to a messenger molecule (310). When the bio-film (120) is subjected to the messenger molecule (310), it produces the first substance (122) and the re-shapeable part of the antenna is subjected to bio-degradation and changes in form. The response, produced by the antenna (110) by reflecting of the electromagnetic signals falling on the antenna, changes because of bio-degradation and thus, a distinguishable signal related to the presence of the messenger substance is produced.

Provided that it is not delimiting, the messenger molecule (310) mentioned in this embodiment as example is the quorum sensing molecule related to a bacteria infection. The genetically engineered microorganism (121) is the Coli Bacilli strain which produces/secretes acidic acid as the first substance (122) when it is subjected to said quorum sensing molecule. The re-shapeable part can be a conductor comprising magnesium but not limited with this. Acidic acid secreted from the bio-film (120) provided around the re-shapeable part increases the bio-degradation speed of the re-shapeable part.

Figure 4:
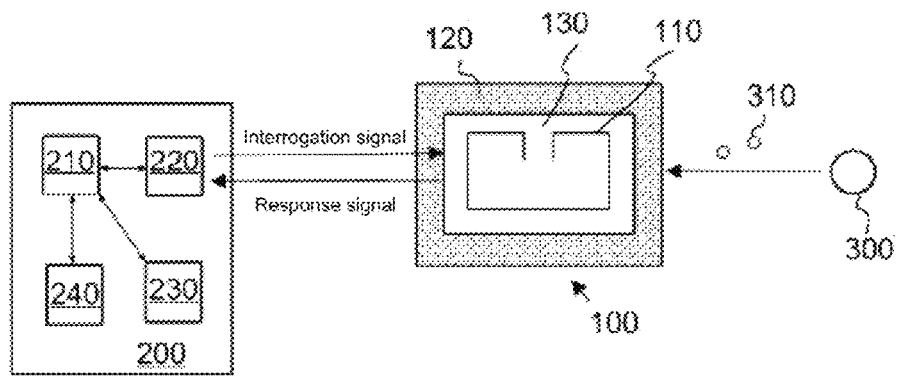
FIG. 4 is a representative view of a possible embodiment of the communication unit, where the communication unit comprises bio-film, which transmits data from inside the body to outside of the body and the system comprising said communication unit, for usage inside the body.

With reference to FIG. 4, the molecular communication unit (100) can also comprise a substrate (130) which wraps the antenna for decreasing the speed of bio-degradation at least partially. Thus, the lifetime of the antenna inside the body is increased and data can be taken for longer time. In a possible embodiment, the antenna is provided between two substrates (130). At the same time, the substrate (130) facilitates placement of the antenna into the body. Said substrate (130) can comprise at least one of polyglycerol sebacate, polyoctamethylene meleate (anhydrite) citrate, polylactic acid and poly(lactic-co-glycolic acid).

Figure 5:
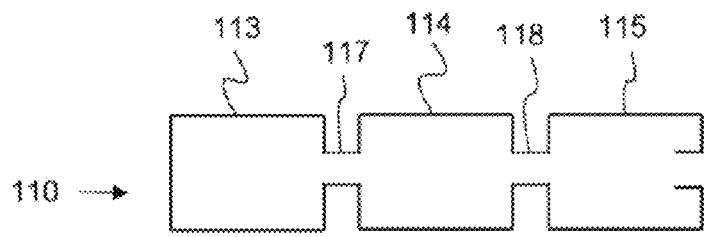
FIG. 5 is a representative view of a possible embodiment of the communication unit which transmits data from inside the body to outside of the body, where said embodiment provides transfer of data in a stepped manner, and the system comprising said communication unit, for usage inside the body.

With reference to FIG. 5, in a possible embodiment of the present invention, the antenna body (111) comprises a first part (113), a second part connected to said first part (113) by means of a first re-shapeable part (117) and a third part connected to said second part (114) by means of a second re-shapeable part (118). The first re-shapeable part (117) and the second re-shapeable part (118) are wrapped by means of substrates (130) made of different materials or having different thicknesses and the bio-degradation can be realized in a stepped manner. The first re-shapeable part (117) and second re-shapeable part (118) can be subjected to bio-degradation in different conditions and in different times and thereby, the same antenna can be used for longer time and can transmit more data. In another possible embodiment of the present invention, the first re-shapeable part (117) and the second re-shapeable part (118) can be arranged in a manner responding to different factors in the body. Thus, data flow related to pluralities of factors by means of an antenna can be provided.

Figure 6:
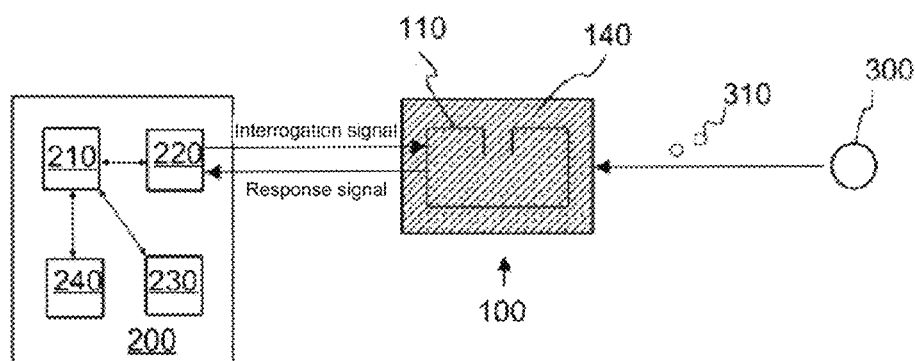
FIG. 6 is a representative view of a possible embodiment of the communication unit which transmits data from inside the body to outside of the body, where said embodiment provides transmission of data in a deformed manner by means of a genetically engineered tissue, and the system comprising said communication unit, for usage inside the body.

With reference to FIG. 6, the molecular communication unit (100) comprises an antenna having an antenna body (111) and re-shapeable part provided in said antenna body (111). Said re-shapeable part is made of a material which changes the physical form when force is exerted. In more details, it is made of a material which changes its physical form when force is exerted and which recovers its physical form when the exerted force is removed. The molecular communication unit (100) comprises a genetically engineered tissue (140) provided in the vicinity of the antenna body (111) for changing the form of the antenna body (111) when it is strained. Said genetically engineered tissue (140) can be a tissue obtained by changing the genetic of the sample muscle tissues taken for instance from insects. When the genetically engineered tissue (140) meets a messenger molecule (310), it strains and provides the re-shapeable part of the antenna body (111) to be deformed and provides the resonance frequency of the antenna body (111) to be changed and provides data transfer from the inside of the body to the outside of the body.

In a possible embodiment of the present invention, the genetically modified tissue (140) is the myocardium. The antenna (110) is produced together with the genetically modified myocardium such that its shape can be deformed by, and afterwards the antenna (110) is placed to human body. The dimensions of the antenna change rhythmically together with the rhythm of the muscle so that the reflected signal's amplitude has two states: high and low. This can be modeled such that the received signal multiplied with a square wave with a frequency of the heart muscle. When the genetically modified myocardium is subjected to messenger molecules, it changes the rhythm and thus, the frequency of the multiplication signal is changed. Thus, the processor unit (210) takes data from the antenna by means of frequency modulation.

In other words, the genetically engineered myocardium operates as a switching mixer and modulates the signal reflected from the antenna placed inside the human body. The straining frequency of the muscle is going to be equal to the frequency of switching. In a similar manner to the phenomenon where the rhythm of human myocardium changes by means of adrenaline, the rhythm of the genetically modified myocardium can be changed by means of the messenger molecule to be used in molecular communication. Thanks to this, as in the frequency shifted switching method, the frequency (f1=f0+fheart or f2=f0+fexcited_heart) of the signal reflected as a result of multiplication with the heart muscle frequency and the frequency (f2=f0+fheart') of the signal reflected as a result of multiplication with the genetically modified myocardium without and with the presence of the messenger molecule correspond to Space and Mark frequencies.

In this possible embodiment of the present invention, this material is gold. In alternative embodiments, different materials having this characteristic can also be used.

The mentioned force which provides change of the physical form and recovery of the physical form describes a force produced by a genetically engineered tissue, which can change the physical form of an antenna body (111) such that the resonance frequency of said antenna body (111) can be changed. This force and the material which will be flexible against this force show variation according to the type of the tissue and the form and thickness of the antenna body (111).

Figure 7:
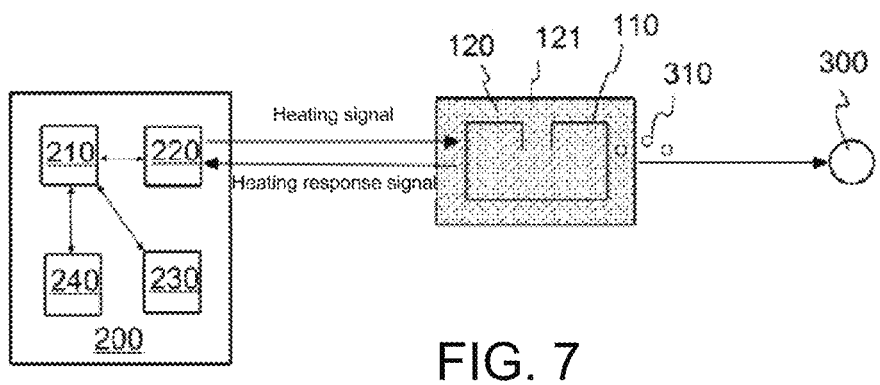
FIG. 7 is a representative view of the communication unit which transmits data from inside the body to outside of the body and the system comprising said communication unit, for usage inside the body.
Figure 8:
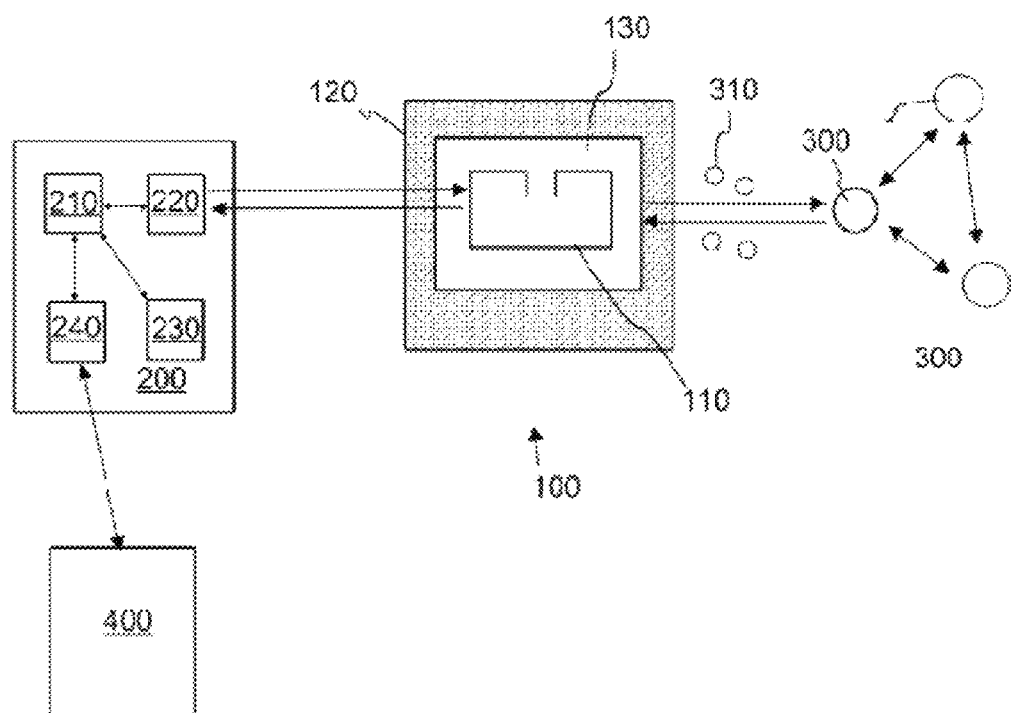
FIG. 8 is a more detailed representative view of the subject matter system for usage inside the body.

In FIG. 7, the view of the molecular communication unit (100) which transfers data from the other communication unit (200) outside the body to the nano-elements (300) inside the body or on a region of the body. The other communication unit (200) comprises an antenna made of the bio-degradable material which has a structure which transmits data from the inside of the body to the outside of the body, and a bio-film (120) which wraps the antenna. When the bio-film (120) in the genetically engineered microorganism (121) reaches a predetermined temperature, it secretes messenger molecule (310). Said genetically engineered microorganism (121) can be *Coli* bacilli comprising initiator with heat activation. For instance, when the *coli bacillus* reaches 45 degrees, it may secrete a protein which functions as messenger molecule (310). Various microorganisms known in the art can be used as the genetically engineered microorganism (121) used in the bio-film (120). It can be used in various fields according to the secreted messenger molecule (310). Since the messenger molecule (310) is sent to the nano-elements (300), communication can be realized and at the same time, this characteristic can be used for treatment.

The other communication unit (200) of the system provides transmission of interrogation signal to the antenna by means of the receiver/transmitter (220) by the processor unit (210) for heating of the bio-film (120) in the molecular communication unit (100). The processor unit (210) determines the present resonance frequency of the antenna according to the response signal received from the interrogation signal. When it is desired to transmit data to the nano-elements (300) afterwards, the processor unit (210) transmits an electromagnetic signal for heating purposes to the antenna by means of the receiver/transmitter (220) at the detected resonance frequency. The antenna reflects the received heating signal and provides heating of the periphery thereof with the effect of the microwave effect. When the periphery of the antenna is heated and as the temperature is reached where the bio-film (120) of the engineered microorganism (121) secretes the messenger molecules (310), and provides the part of the communication which is from the outside of the body to the inside of the body to be completed.

While the temperature of the medium increases the bio-degradation speed of the re-shapeable part in the antenna body (111) also increases. The processor unit (210) monitors the rate of degradation and decides if the target temperature has been reached to stop the heating process.

Figure 9:
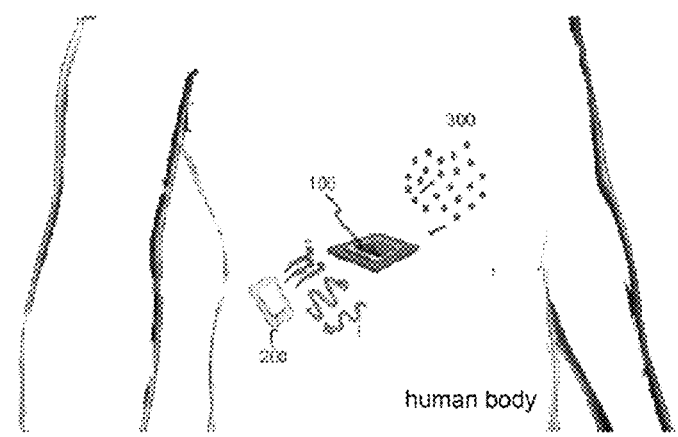
FIG. 9 is a representative view where the other communication unit is connected to human body externally and where the molecular communication unit is placed into the body, for usage inside the body.

When the molecular communication unit (100) is placed into the body, the other communication unit (200) is approached to the molecular communication unit (100) and data exchange is easily provided. With reference to FIG. 9, in a possible embodiment, the other communication unit (200) is provided in a form which can be adhered to the body. Thus, data exchange can be realized continuously and the patients can be easily monitored.

Figure 10:
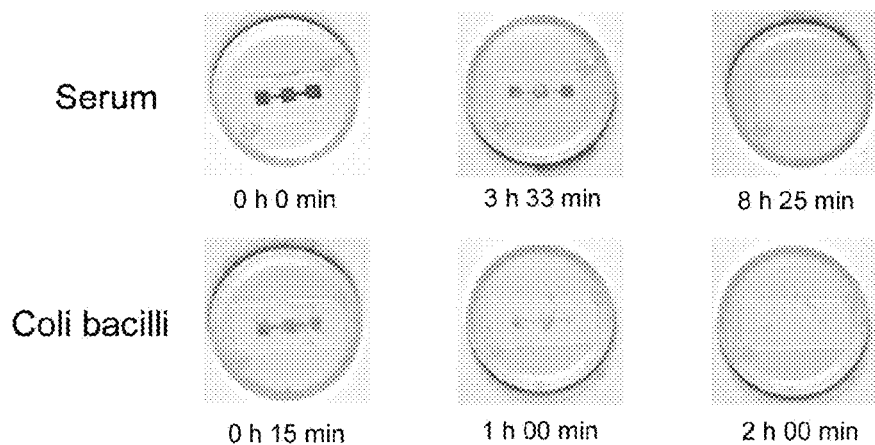
FIG. 10 is a representative view of the measurement of degradation speed of the bio-degradable material placed into serum and the bio-degradable material placed into the serum including coli bacilli.

In FIG. 10, the comparison of the degradation speed of the magnesium samples placed into serum and the magnesium samples placed into the serum including coli bacilli is given. Said samples have been produced on glass by means of DC Mg break-off method. It has been observed that magnesium has completely degraded in serum in approximately 8 hours, and it has been completely degraded in serum including coli bacilli. This shows that the bacterial activity of *coli* bacilli increases degradation speed.

Figure 11:
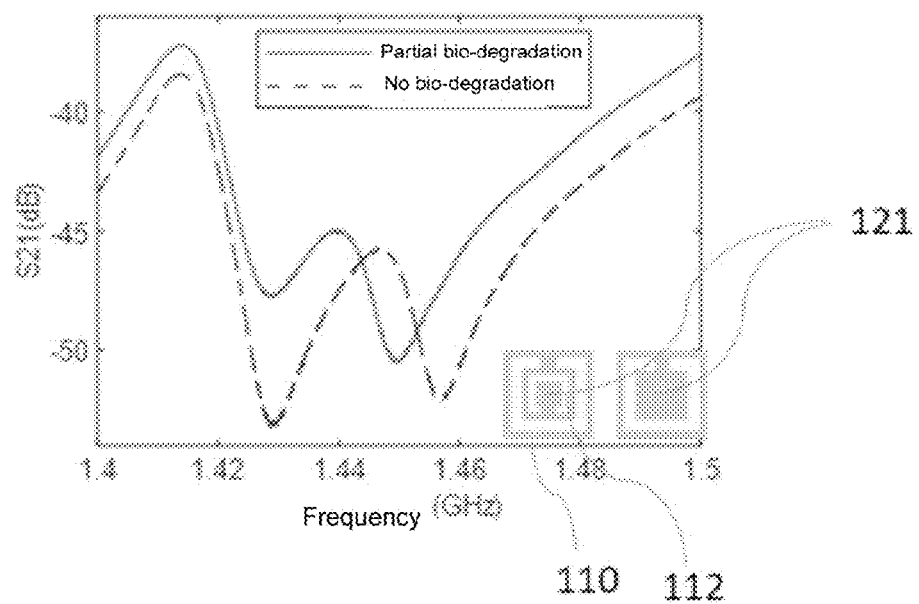
FIG. 11 is S21—parameter—frequency measurement graphic including monitoring by means of electromagnetic waves by degradation of materials of which the bio-degradation speed is given in FIG. 10.

Since degradation is associated with bacterial activity and thanks to the genetically engineered microorganism (121) and with controllable bacterial activity by means of a specific molecule, the degradation can be associated with the presence of said molecule. Change of the resonance frequency as the antenna (100) (resonator) placed into the body degrades and monitoring of this change by means of wearable antennas which exist outside the body provide the molecular communication to be connected to electromagnetic communication. In FIG. 11, the measured frequency response of an antenna, placed into the serum, with the other communication unit (200) prior to degradation and during degradation (after the re-shapeable part (112) degrades) is seen.

This shows that the electromagnetic signal reflected by the antenna (110) changes since the re-shapeable part changes in form when it is subjected to a factor inside the body. Thus, the information related to this change is transferred from inside or on the body to the outside of the body.

The protection scope of the present invention is set forth in the annexed claims and cannot be restricted to the illustrative disclosures given above, under the detailed description. It is because a person skilled in the relevant art can obviously produce similar embodiments under the light of the foregoing disclosures, without departing from the main principles of the present invention.

What is claimed is:

1. A system for receiving data from nano-elements in a body, comprising a first molecular communication unit, wherein the molecular communication unit comprises an antenna to be attached into the body or on the body for transferring the data from a molecular nano communication network to a body area network, and the antenna comprises an antenna body configured to transform and reflect an electromagnetic signal when the antenna body is exposed to the electromagnetic signal, and the antenna body comprises a re-shapeable part made of a material changing in form when the antenna body is subjected to a factor inside the body.

2. The system according to claim 1, wherein second molecular communication unit is provided having a receiver/transmitter for transmitting the electromagnetic signal to the antenna and for receiving the electromagnetic signal reflected by the antenna and a processor unit configured to control transmission of the electromagnetic signal to the antenna by the receiver/transmitter (220) and to receive the electromagnetic signal received from the receiver/transmitter, and the processor unit is configured to determine whether the antenna is subjected to the factor inside the body according to at least one characteristic property of the electromagnetic signal received from the antenna.

3. The system according to claim 2, wherein the at least one characteristic property is a frequency.

4. The system according to claim 2, wherein the second molecular communication unit comprises a memory unit provided in an associated manner with the processor unit in a manner permitting reading data by the processor unit; and the processor unit is configured to determine whether the antenna is subjected to the factor inside the body according to a deviation of the at least one characteristic property of the electromagnetic signal received from the antenna, from at least one characteristic property existing in the memory unit.

5. The system according to claim 2, wherein the second molecular communication unit comprises an input output unit providing the processor unit to realize an output related to subjecting of the antenna to the factor inside the body.

6. The system according to claim 2, wherein the second molecular communication unit comprises a body of the second molecular communication unit and the body of the second molecular communication unit is placed inside the body or on the body.

7. The system according to claim 1, wherein a whole of the antenna body is the re-shapeable part.

8. The system according to claim 1, wherein the material changing in form when the antenna body is subjected to the factor in the body is a first bio-degradeable material.

9. The system according to claim 8, wherein a bio-film is provided in a manner at least partially wrapping the re-shapeable part.

10. The system according to claim 9, wherein the re-shapeable part comprises a material with a bio-degradation speed increasing when the material is subjected to a first substance.

11. The system according to claim 10, wherein the system further comprises a genetically engineered microorganism for generating the bio-film, and the bio-film generates the first substance when subjected to a messenger molecule.

12. The system according to claim 11, wherein the first substance is an acidic acid.

13. The system according to claim 12, wherein the messenger molecule is a quorum sensing molecule related to a bacteria infection and when the genetically engineered microorganism is subjected to the quorum sensing molecule, a Coli Bacilli strain produces the acidic acid as the first substance.

14. The system according to claim 8, wherein the first bio-degradeable material is selected from the group consisting of magnesium, iron, and double-layered zinc/iron.

15. The system according to claim 8, wherein at least one substrate is provided in a manner at least partially wrapping the antenna for decelerating a degradation speed of the re-shapeable part.

16. The system according to claim 15, wherein the at least one substrate comprises a second bio-degradeable material.

17. The system according to claim 16, wherein the at least one substrate comprises at least one of polyglycerol sebacate, polyoctamethylene meleate (anhydrite) citrate, polylactic acid, and poly(lactic-co-glycolic acid).

18. The system according to claim 16, wherein two substrates are provided such that the antenna is received between the two substrates.

19. The system according to claim 8, wherein the antenna body comprises a first part, a second part connected to the first part by a first re-shapeable part, and a third part connected to the second part by a second re-shapeable part.

20. The system according to claim 19, wherein the first re-shapeable part and the second re-shapeable part are made of second bio-degradeable materials, the second bio-degradeable materials are degraded when they are subjected to factors which are different from each other.

21. The system according to claim 19, wherein the first re-shapeable part and the second re-shapeable part are coated with substrates having bio-degradation speeds different from each other.

22. The system according to claim 21, wherein for adjusting the bio-degradation speeds of the substrates, a coating thickness is selected from one of predetermined thicknesses in accordance with a targeted degradation speed.

23. The system according to claim 1, wherein the re-shapeable part is configured to bend when the re-shapeable part is subjected to a force exceeding a predetermined threshold value.

24. The system according to claim 23, wherein a genetically engineered tissue is provided and related to the re-shapeable part, and the genetically engineered tissue provides a deformation of the re-shapeable part by straining and by applying a force to the re-shapeable part when the re-shapeable part is subjected to a messenger molecule.

25. The system according to claim 24, wherein the genetically engineered tissue is a muscle tissue.

26. The system according to claim 1, wherein a bio-degradable capsule is provided and placed inside or on the body for providing information transfer from outside of the body to inside of the body or onto the body and the bio-degradable capsule comprises messenger molecules configured to be used in a molecular communication, and when a wall of the bio-degradable capsule is subjected to the electromagnetic signal sent from outside of the body, the messenger molecules are released due to an increase in heat.

27. A method for receiving data from nano-elements from a body, comprising the steps of:
transmitting, by a processor unit, an interrogation signal to an antenna having an antenna body configured to reflect an electromagnetic signal when the antenna body is subjected to the electromagnetic signal by a receiver/transmitter and a re-shapeable part made of a material changing in form when the antenna body is subjected to a factor inside the body, receiving, by the processor unit, a response signal, wherein the response signal is produced by reflecting the interrogation signal by the antenna, by a receiver/transmitter, determining, by the processor unit, whether the antenna is subjected to the factor inside the body according to a deviation of characteristic properties of the response signal from predetermined reference characteristic properties.

28. A system for transferring data to nano-elements communicating with messenger molecules inside a body, wherein a molecular communication unit is provided to be attached to the body and having a bio-film and accommodating a genetically engineered microorganism, the genetically engineered microorganism is heated when the molecular communication unit is subjected to an electromagnetic signal and produces the messenger molecule when a predetermined temperature level is reached.

29. The system according to claim 28, wherein an antenna is provided and configured such that when the antenna is subjected to the electromagnetic signal, the antenna reflects the electromagnetic signal.

30. The system according to claim 29, wherein an external communication unit is provided having a receiver/transmitter for transmitting the electromagnetic signal to the antenna and for receiving the electromagnetic signal reflected by the antenna and a processor unit configured to control a transmission of the electromagnetic signal to the antenna by the receiver/transmitter (220), and when the data is to be sent to the nano-elements, the processor unit is configured to detect a resonance frequency of the antenna according to a response signal of the antenna reflected in correspondence with an interrogation signal sent by the receiver/transmitter and to transmit an electromagnetic heating signal for heating purposes to the antenna in continuous and monolithic form at the resonance frequency detected.

31. The system according to claim 30, wherein the antenna is made of a bio-degradeable material with increasing bio-degradation speed as temperature increases, and the processor unit is configured to receive a response heating signal, the response heating signal is a reflected form of the electromagnetic heating signal and to stop a transmission of the heating electromagnetic signal in case the processor unit detects that characteristic properties of the response heating signal deviates from predetermined reference characteristic properties at a predetermined amount.

32. A method for transferring data to nano-elements communicating with messenger molecules inside a body, comprising the steps of:

receiving, by the processor unit, a data transfer command as an input, transmitting, by the processor unit, an electromagnetic wave to an antenna reflecting the electromagnetic wave reflected falling thereon, when the electromagnetic wave falls thereon by a receiver/transmitter, determining, by the processor unit, a resonance frequency of the electromagnetic wave reflected by the antenna by the receiver/transmitter, transmitting, by the processor unit, a continuous and monolithic electromagnetic signal to the antenna at a determined resonance frequency for increasing a temperature of a bio-film of a genetically engineered microorganism provided in a vicinity of the antenna and producing a messenger molecule when the temperature increases to a predetermined level at the determined resonance frequency.

33. The method according to claim 32, wherein an antenna body of the antenna is made of a bio-degradeable material with an increasing degradation speed in case of a temperature increase and the processor unit receives a response signal produced by reflecting the continuous and monolithic electromagnetic signal at the determined resonance frequency by the antenna by the receiver/transmitter, the processor unit stops a transmission of the continuous and monolithic electromagnetic signal in case the processor unit detects that the characteristic properties of the response signal deflect from the predetermined reference characteristic properties at a predetermined amount.

\* \* \* \* \*